United States Patent [19]

Pallotta

[11] 4,373,819

[45] Feb. 15, 1983

[54] RETROREFLECTOMETER GIVING DIRECT READING

[76] Inventor: Stefano Pallotta, Rome, Italy

[21] Appl. No.: 219,390

[22] Filed: Dec. 22, 1980

[30] Foreign Application Priority Data

Dec. 21, 1979 [IT] Italy .............................. 51179 A/79

[51] Int. Cl.³ ........................................... G01N 21/55
[52] U.S. Cl. ................................................. 356/445
[58] Field of Search ............................... 356/445–448, 356/429, 430, 369, 237, 238, 371; 250/571, 572, 559, 562

[56] References Cited

U.S. PATENT DOCUMENTS 2,739,246  3/1956  Hunter ................. 250/571

FOREIGN PATENT DOCUMENTS 2258617  8/1975  France .......................... 356/445

OTHER PUBLICATIONS

U.S. Defensive Publication, No. T987,003, issued to Johnson et al., dated Oct. 2, 1979, filed Jul. 31, 1978.

*Primary Examiner*—Bruce Y. Arnold

*Attorney, Agent, or Firm*—McGlew and Tuttle

[57] ABSTRACT

The invention concerns an improved retroreflectometer giving direct readings for measuring the value or degree of retroreflectivity, or visibility at night, of a paint applied to the surface of the road for marking ground signs, under conditions that simulate geometrically the real conditions of illumination and visibility of the sign from the driver of a vehicle. The value or degree of retroreflectivity is measured directly from the sample in question, making it unnecessary to have a sample for comparative purposes and, as a result, eliminating the need to zero the apparatus before each measurement is taken. Provision is made for varying the angle at which the light beam strikes the sample, so as to simulate the actual conditions produced by different heights and/or degrees of inclination of the headlights of different categories of vehicles, and to vary the degree of inclination of the detecting element in relation to the retroreflected beam, so as to simulate the visual angle of the driver, and thus alter the angle of divergence, or phase displacement angle, between the incident beam and the retroreflected beam. The detected data are processed, stored and transduced, so as to be readable on a known type of display.

7 Claims, 5 Drawing Figures

RETROREFLECTOMETER GIVING DIRECT READING

The products normally used for horizontal and/or vertical signs on roads, at airports, and so forth, essentially are paints characterized by the fact that they incorporate materials that are to a greater or lesser degree geometrically defined, for example, glass microbeads, suitable to send back to a source of light a proportion of the quantity of light contained in the incident beam sent out by the source itself.

In optical physics this phenomenon is described as "retroreflectivity" and in sign marking technology the quantity of light retroreflected represents the nocturnal visibility of the sign when subjected to the light from headlights of moving vehicles (motor cars, and more generally, aircraft when taxiing or making visual landings).

The problem therefore arises, both in the research and design stage and in the construction of signs, as well as in the checking of their state of conservation and efficiency, of measuring the degree of retroreflectivity, or in other words the nocturnal visibility, of the products applied to the road surface to produce the signs such as, for example, the continuous or broken lane markings, "stop" lines and so on.

Such checks and measurements must be carried out in reproducible conditions so as to enable the data to be compared without any subjective evaluation by the operator. Apparatus for measuring retroreflectivity are known which effect the measurement by comparison between the quantity of light retroreflected by the product sample being tested and the one retroreflected by a standard sample, for example of an opaque white color, with both samples being illuminated under conditions geometrically similar to the conditions of visibility from the drivers of vehicles, taking into account the angle of divergence between the incident beam or ray of light and the retroreflected beam or ray of light. The intensity of the retroreflected ray is detected by a photo-electric cell and the retroreflectivity value is read on a measuring instrument connected to it. Such well known types of retroreflectometers, however, present numerous disadvantages that are avoided by means of the improved retroreflectometer giving direct readings according to the present invention.

(a) In the known retroreflectometers, the incident ray and the reflected ray are concentrated and guided by means of optical systems using lenses, prisms, mirrors and so forth, which substantially alter the comparison between the geometrical conditions of illumination of the sample obtained inside the apparatus and the actual conditions of visibility from the vehicle drivers.

(b) The measurement of the degree of retroreflectivity is influenced by the comparison with a sample that is not standardized in accordance with conventionally recognized norms. Anyway, the change, for example, as the result of deformations and/or for the presence of extraneous materials such as dust, grease, and suchlike, and/or by chromatic alterations. Thus, not only the data measured by different types of apparatus are unfit to be compared one with another, and hence indexed, but the same is equally true for the data measured with the same type of apparatus, or, in the extreme, using the same apparatus itself but at different times. In addition, before they can be used, such known types of apparatus have to be zeroed in relation to the sample, checking the state of cleanliness and/or conservation and the exact positioning of the comparative sample, operations which are influenced by the operator and tend to diminish the reliability of the data measured, to the disadvantage of the reproducibility of the measurement.

(c) The angles of the incident ray and the retroreflected ray are fixed, which means that it is not possible to adapt the instrument for taking measurements under different conditions of visibility such, for example, as correspond to the actual conditions of visibility from the driver of a car or truck, or the conditions of visibility corresponding to the use of fog lights or those of a pilot at the controls of an aircraft.

The present invention concerns an improved retroreflectometer giving direct readings, that is easy, practical and economical to construct, and in which the light source, the incident ray and the retroreflected ray are perfectly adaptable to the real conditions of illumination and visibility of a vehicle, without any need for optical systems for focusing and returning the beam of light. In addition, the degree of retroreflectivity is measured directly on the sample under examination, thus eliminating the need for a comparative sample; furthermore, provision is also made for the angle of inclination of the incident ray to be varied, leaving the angle of divergence unchanged, or varying that angle at will, depending on the different operational requirements.

Other features and advantages of the invention will become clear from the following description and attached drawings, in which is shown an illustrative but nonlimiting embodiment of an improved retroreflectometer giving direct readings according to the present invention.

The apparatus according to the invention may be provided with the energy needed to make it work, either from an A.C. mains network or from a battery buffer-connected with the supply circuit, and consisting of a plurality of rechargeable dry cells.

The apparatus consists of a light-proof box or chamber (1) on the underside of which, close to one end, there is a rectangular opening or "window" (2), the perimeter of which is surrounded by a frame (3) of a material that is sufficiently flexible to allow it to fit flush against the surface of the road/or track to prevent infiltration of light into the chamber itself. Alternatively, this frame (3) may consist of a bellows, of the type used in cameras.

The chamber (1) has a raised top on which is a control and reading board, which top should preferably be near the end of the chamber opposite to the "window"(2). Also fitted to the upper side of the chamber is a handle (5) for carrying the apparatus, and two levels (6 and 7) arranged at right angles to one another, for checking that the apparatus is horizontal, both longitudinally and transversely, when on the ground.

For adjusting the apparatus so that it is properly horizontal, screw adjusters of a known type are provided, by means of which the levels can be perfectly centered.

Figure 1:
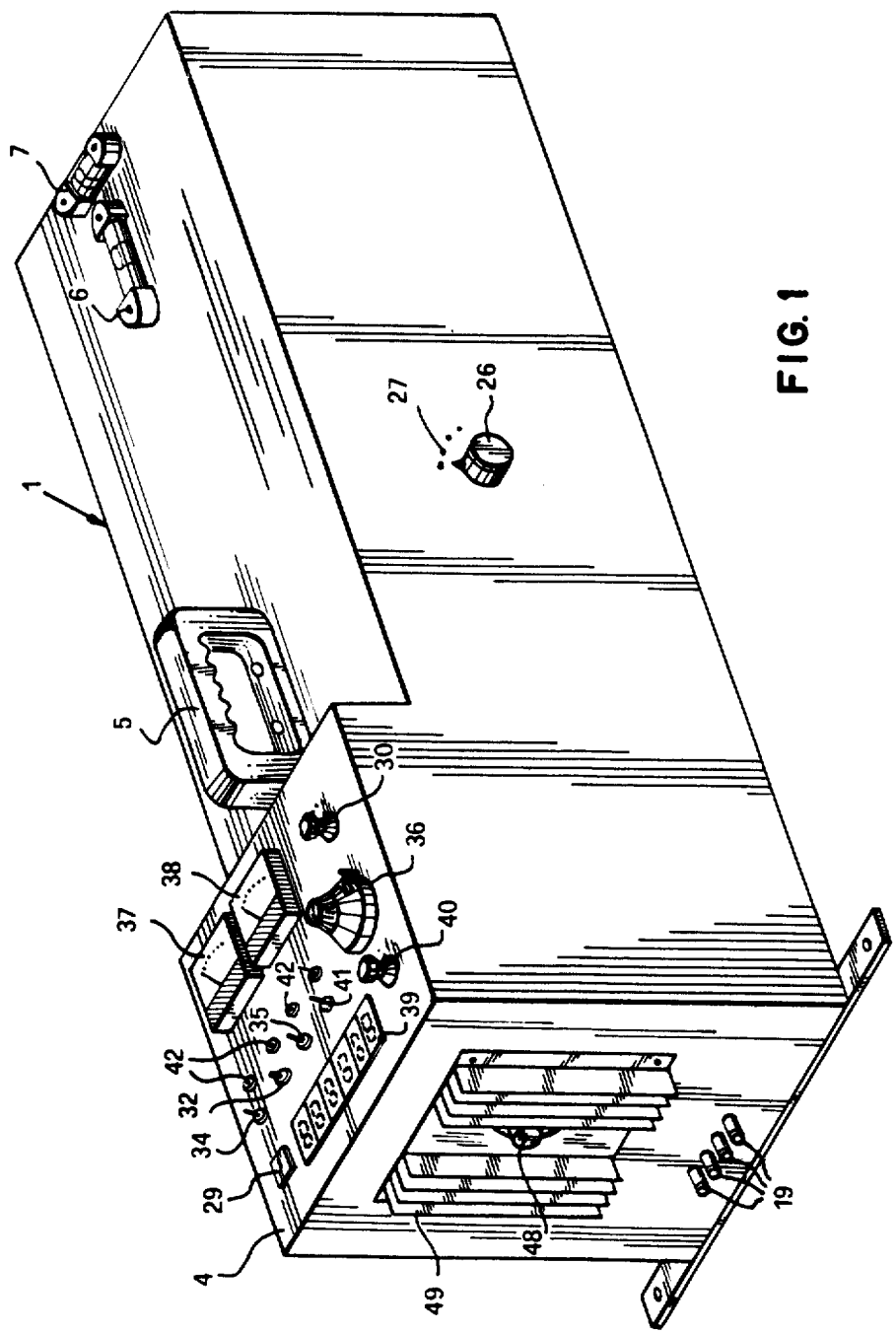
FIG. 1 is an axonometric three-quarters view of an embodiment of a retroreflectometer according to the present invention.
Figure 2:
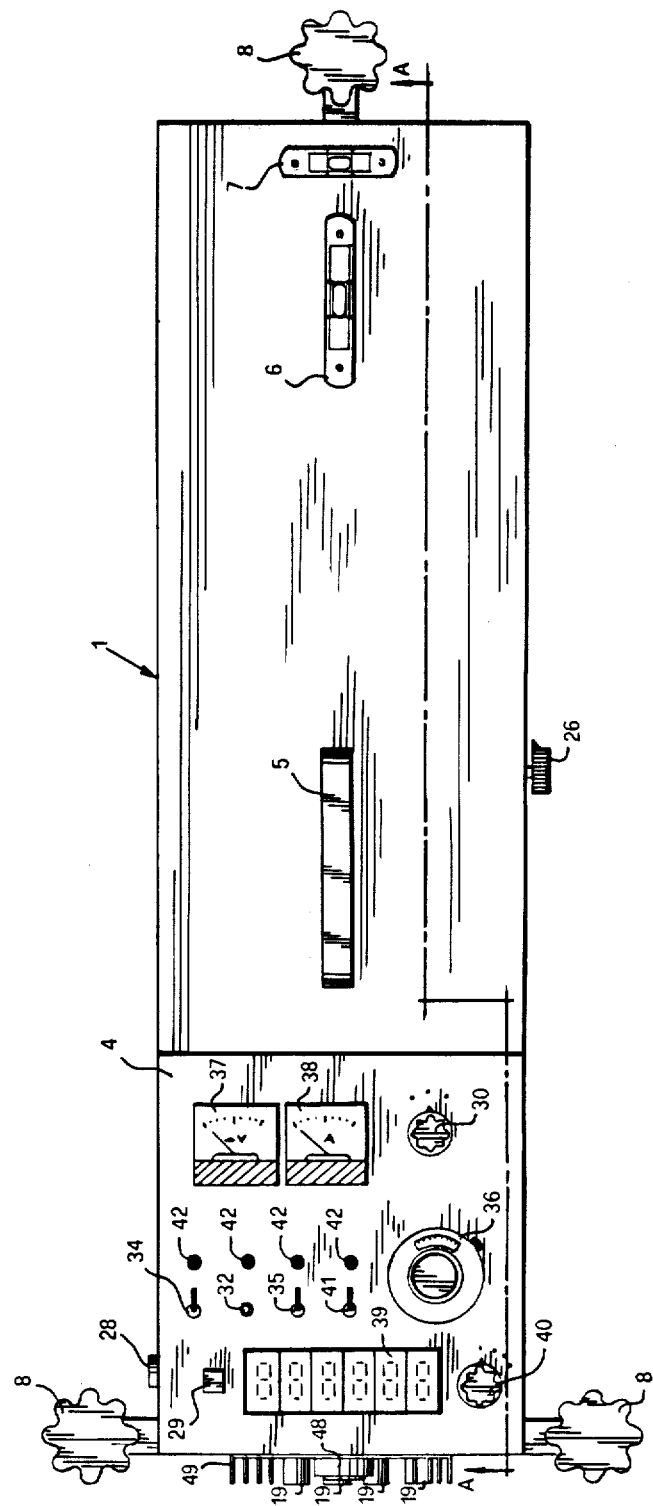
FIG. 2 is a plan view of the retroreflectometer of FIG. 1.
Figure 3:
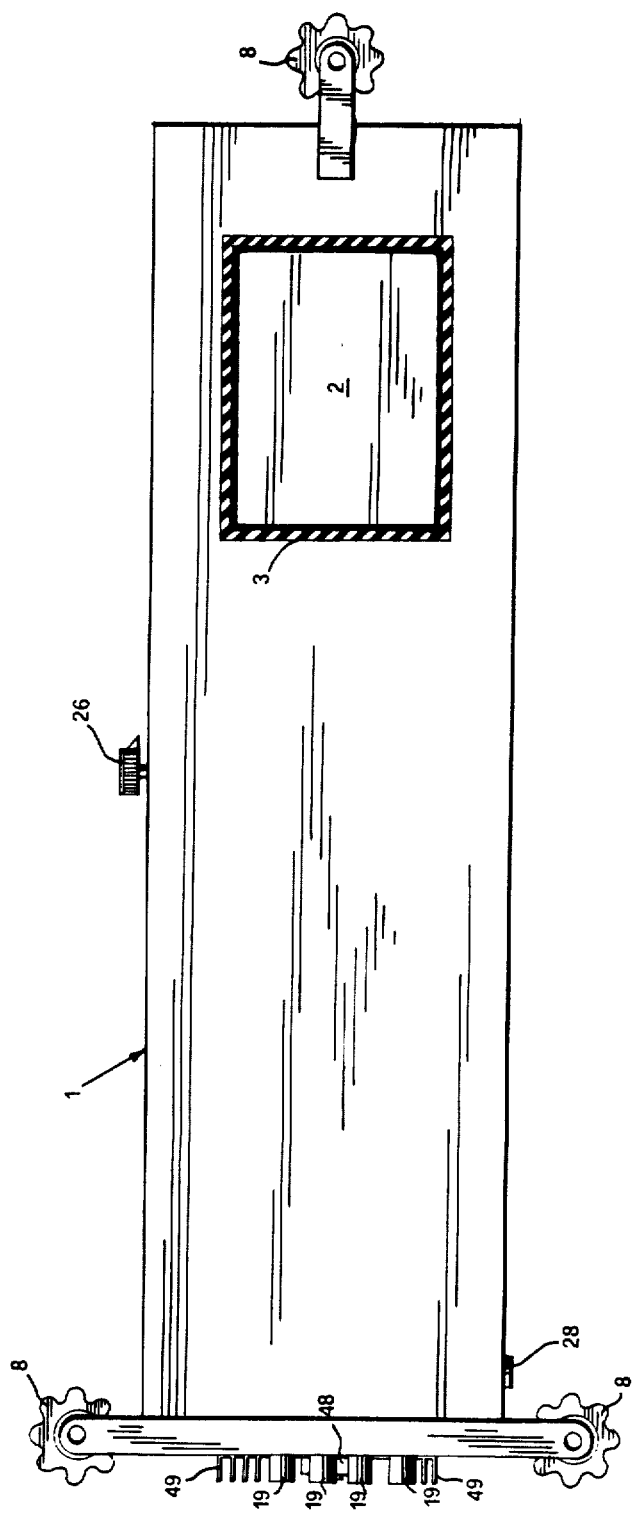
FIG. 3 is a plan view of the bottom of the retroreflectometer of FIG. 1.
Figure 4:
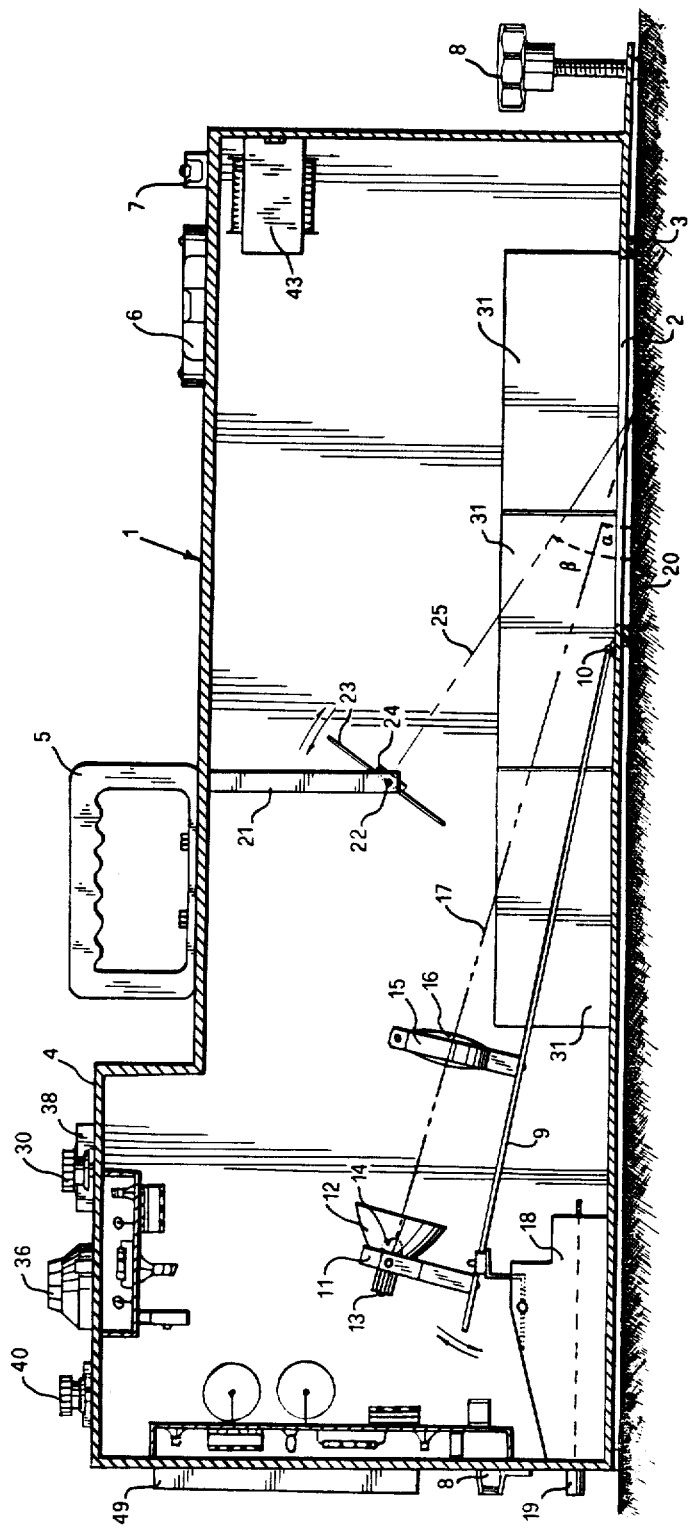
FIG. 4 is a schematic side view of the interior of the retroreflectometer, in section taken along the dotted line A-A of FIG. 2.

As shown in FIG. 4, inside the chamber (1) a rigid rod (9) is attached to a hinge (10) fixed to the base of the chamber (1) and can pivot about on the hinge pin. On the rod is fixed the bracket (11) of a parabolic reflector (12) with a socket (13) for a bulb (14). The reflecting surface of the parabola (12) should preferably not be specular, but a known pressed kind of surface consisting of a plurality of facets in the form of geometrical figures such as, for example, hexagons arranged in a honeycomb pattern, so as to keep the amount of light flow equal, as far as possible, to the amount of light emitted.

On the rod (9) between the parabola (12) and the hinge (10) there is a holder (15) for a convergent lens (16), placed along the light path at a predetermined distance from the light source, so as to direct onto the "window" (2), which is placed over the sample (20) to be measured, the maximum quantity of emitted light, by avoiding dispersion and reducing the optical distance between the light source and the "window".

The known apparatus provide an inclination of the incident ray of light at around 3°–4°, whereas in reality the inclination of the beam of light from a vehicle's headlight, measured between the focal centre of the parabola, and the point which experimentally corresponds with the centre of the zone of maximum luminance, varies from 9°–11°.

In addition, such known apparatus do not take into account the fact that conditions of visibility, as we have already said, vary for the different driving positions found in different vehicle categories.

To overcome these difficulties, the apparatus according to the present invention is conceived so as to allow the inclination of the incident beam or ray of light, represented ideally by the broken line (17) to be varied, so as to give a number of different predetermined angles which can be calibrated when the apparatus is assembled and/or adjusted, thereby avoiding the risk of operational errors. The inclinations may be selected so as to simulate the real conditions corresponding to different heights and/or inclinations of the light sources, i.e. different heights and/or inclinations of the headlights of different categories of vehicles such as, for example, motor cars, heavy vehicles, aircraft, etc., and/or to different types of headlights such as, for example, headlights on main beam, headlights with low beam, fog lights, and so on.

For this purpose the rod (9) supporting the parabolic reflector (12) and convergent lens (16) used to focus the light source, is pivotable about the axle of the hinge (10) so that the rod (9) can be adjusted to give the inclinations required, for example 11°, 13.5° and 16°.

The changeover from one angle of inclination to another is effected by means of a selector (18) consisting of a mechanical and/or electromechanical device, which may be of a known type and which may be controllable from outside the chamber (1) by means of push-buttons (19) three of which, for example, correspond to three different, predetermined angles of inclination of the rod (9), whilst the fourth, when pressed, can be rotated on its axle and it is used for carrying out the calibrating operations and/or the selection of a different combination of angles of inclination. When this button is released it remains locked in position, so as to avoid accidental alteration and/or modification of the calibration.

Inside the chamber (1) there is a bracket (21) in the form of an inverted U, in which is rotatably mounted a horizontal axle (22) supporting a small plate (23) provided to support at least one photo-electric cell (24) in positions suitable to receive the retroreflected beam, ideally represented by the broken line (25).

The axle (22) can be rotated from the outside by means of a knob (26) to which it is fixed. This knob (26) is locked in predetermined positions correlated to the different angles of inclination of rod (9)—that is to say, the incident ray—and the pointer on the knob works against a graduated scale (27), which scale is subdivided, for example, into degrees and fractions of a degree, corresponding to the angle of inclination of the plate (23).

A clutch built into the knob (26) enables the angles of inclination to be calibrated, and/or a different combination of inclinations of plate (23) to be selected. In this way, just as provision is made for varying the inclination of the incident ray, so, in the apparatus according to this invention, there is provision for varying the inclination of the photo-electric cell (24) in relation to the retroreflected ray (25), thus altering the angle of divergence, or phase displacement angle ($\beta$-$\alpha$) between the incident ray and the retroreflected ray. The angle ($\beta$) is the angle between the retroreflected ray and the horizontal.

The photo-electric cell (24) should preferably, though not necessarily, be situated so that the length of the retroreflected ray that strikes it is half the distance from the lens (16) to the intersection of the diagonals of the sample surface to be measured (20), as bounded by the "window" (2); in this way the photo-electric cell (24) receives quite a small cone of retroreflected light, thus eliminating the need to use optical systems, which would undoubtedly absorb part of the flow of light, and thus diminish the reliability of the measured data.

The attached drawings show a tap (28) for connecting the apparatus to an A.C. mains network, and a push-button switch (29) with built-in pilot light, for switching the mains current on and off.

In addition, there is a function switch (30), one of the functions being provided to supply current to the apparatus from the mains network, and another to supply current only to the recharge circuit for a battery of cells (31) which is built into the apparatus and which, during operation, is buffer-connected; another push-button (32) operates a timer (33) which makes the lamp (14) light up for a fixed time; the timer (33) can be switched off by means of a two-position switch (34). There is also another two-position switch (35) by means of which the operator can switch on the lamp (14) for any period of time required, when switch (34) is in the "off" position.

Furthermore there is provided a control knob which can be locked in any position, for a micrometric variator (36) of the light intensity of the lamp (14); a voltmeter (37) for reading the actual voltage during measuring operations, or the actual voltage of the cells (31) when they are being recharged; a milliammeter (38) for measuring the electrical input of the lamp (14), and hence its luminous intensity, as well as the recharge current for the cells (31); a display (39) of a known type—for example a variable sensitivity digital display—for reading the observed values, and finally, a control knob (40) for operating a full scale variator for the display, which can be used with reading stability up to the second decimal place.

A two-position switch (41) connects the display (39) to (or cuts it off from) the circuit of the apparatus, and there are pilot lights (42) to show when their respective switches (43), (35), (41)—and the push-button (32) of the timer (33)—are switched on.

Figure 5:
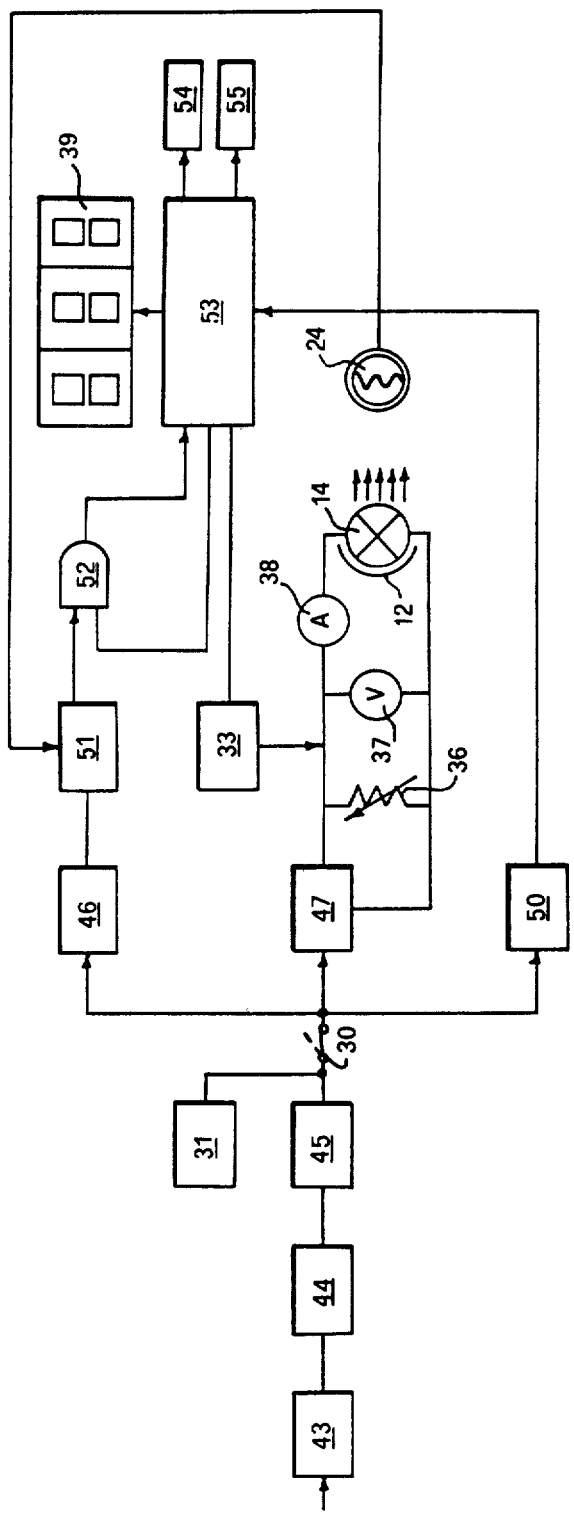
FIG. 5 is a block diagram of a supply and measuring circuit of the retroreflectometer of FIG. 1.

Referring to the block diagram in FIG. 5, the A.C. mains voltage—200 V for example—is reduced to 25 V by means of the transformer (43) and converted into D.C. by means of a rectifier (44) and filter (45). The battery of cells (31) is buffer-connected to the output from the filter (45) and, downstream of this connection, there is a function switch (30). When this switch is in the operating position, the output current is divided into three branches, as follows: one goes to block (46), which represents a ±15 V dual integrated circuit voltage stabilizer, with current and temperature protection; one goes to block (47) which represents a series regulator integrated circuit 0-25 V stabilizer, with current and temperature protection, which controls a power transistor (48) situated on the outside and equipped with a cooling radiator (49); and one goes to block (50) which represents an integrated circuit +5 V stabilizer, with power and temperature protection.

The output from block (46) is connected to block (51). The function of block (46) is to convert the voltage into frequency, and which is connected in parallel to the photo-electric cell (24).

When the chamber (1) is in darkness, the photo-electric cell (24) has a high input voltage, and inhibits the voltage-frequency converter (51). On the other hand, when the photo-electric cell (24) is excited by the retroreflected ray (25) the input voltage falls and allows the converter (51) to function in a linear mode, with an output of trains of impulses that vary according to the input voltage level—that is, the greater or lesser intensity of the retroreflected ray detected by the photo-electric cell (24).

The impulses at the output of the electronic switch represented by block (52), which is activated for the time determined by the timer (33), are then in succession filtered, counted, decoded and stored by the logic control circuit represented by block (53) and thus made available for the display (39). As an option there is an interface (54) for recording the measured data, for example on a cassette and/or via a printer, and a second interface (55) for teletransmission of the measured data.

As FIG. 5 shows, by means of the micrometric variator (36) in the output circuit from block (47) the electrical input of the lamp (14), and hence its light intensity, can be varied.

This is necessary, since the light intensity of the lamp and the time for which the lamp is on (the flash), which is controlled by the timer (33), are the fundamental parameters which must remain constant for the measurements to be reproducible.

If one of the two parameters is altered, for example the time for which the lamp is on with the same light intensity, the retroreflectivity readings now obtained would not correspond with readings previously obtained with the apparatus calibrated on the basis of optimum light intensity and optimum exposure time, as experimentally determined, since, if the time is increased, the photo-electric cell would finish up by recording spurious forms of light, such as diffused and reflected light, thereby distorting the value of the retroreflected light.

It should be remembered that the lamp (14) can be changed depending on the lighting conditions it is desired to simulate; for example it can have a different form and/or range of light emission, to which, obviously, different experimental values correspond, determined in the laboratory.

For evaluating the retroreflectivity or nocturnal visibility of the sample to be measured, the retroflectometer according to the present invention may have a reading scale on the display (39) going from 0—corresponding to 100% retroreflectivity—to 10 (EEE)—corresponding to 100% darkness, or black, within the interior of the chamber (1)—, the internal walls of which are opaque black when the apparatus is inactive and the frame (3) is perfectly adherent to the surface of the sample.

In a certain way it can be said that the apparatus so conceived measures the difference in darkness, or blackness, existing inside the chamber before the sample is exposed to the flash of incident light, and during its exposure.

In this way a direct measurement is made of the value of the retroreflectivity of the sample, without the need of comparison with a standard sample, and, consequently, without the need of zeroing the apparatus before taking the measurement, and hence avoiding the risk of operational errors.

In a different form of construction of the invention, the apparatus contains a plurality of photo-electric cells (24) connected in series, each of which is used to measure a portion of the intensity of the retroreflected ray of light, so as to have a selective value for each individual portion, these values being subsequently transduced into cumulative logical values.

This variation enables a more detailed survey of the sample's behavior. In the embodiment of the invention shown as a purely exemplary and non-limiting example, all the elements of the retroreflectometer are combined in a single body, but nothing prevents, for greater convenience in use, the apparatus according to the invention from being constructed in a certain number of parts or sections, as for example by separating from the chamber, with its photo-optical elements and the battery accumulator supply system, all the control and reading instruments which could advantageously be mounted on a portable control panel, connectable to the chamber by means of electrical cables.

Also for greater operating convenience the retroreflectometer could advantageously be fitted to a chassis mounted telescopically on a trolley on rollers or castors, so as to allow the chassis to be raised or lowered right down to the ground, bringing the chamber into contact with the road surface; the mechanism could consist of a rack and sector gear, operated by means of the towing bar and/or hydraulic devices.

I claim:

1. A retroreflectometer giving direct readings, for measuring the value or degree of retroreflectivity of a paint applied to the road surface for marking road signs, and consisting essentially of a light-proof box or chamber (1), essentially prismatic in shape, and having in its under-side a rectangular opening or "window" (2) the perimeter of which has a frame (3) of lightproof, flexible material of a kind that will adhere to the surface to which it is placed, the retroreflectometer comprising: a source of light, consisting of a parabolic reflector (12) and a light bulb (14) mounted on a rod (9) free to move in the vertical plane and attached, at one end, to the spindle of a hinge (10) fixed internally to the base of the chamber (1) near the "window" (2) which bounds the sample (20) to be measured, and a convergent lens (16) also mounted on the rod (9) for the purpose of directing on to the sample (20) the beam or ray (17) of light emitted by the source (12, 14) so as to avoid dispersion, the rod (9) being inclinable in relation to the horizontal to at least 3 predetermined angles of inclination, suitable to be selected by means of a selector (18) that can be set from the outside; at least one photo-electric cell (24) able to receive the retroreflected beam or ray of light (25) from the sample (20) under examination, such photo-electric cell (24) being mounted on a small plate (23) fixed to a rotating axle (22) mounted transversely in respect with the side walls of the chamber (1), and in a position such that the length of the retroreflected ray striking the photo-electric cell is about half the focal length of the lens (16)—so that the photo-electric cell (24) is struck by a cone of retroreflected light sufficiently small to obviate the need for optical focusing and/or return systems—, said plate being capable of being set at at least three predetermined angles of inclination, by means of an external knob (26) which turns the axle (22); the value of degree of retroreflectivity of the sample measured by the photo-electric cell (24) being processed, stored and transduced and so made available for reading on display (39).

2. A retroreflectometer according to claim 1, wherein the source of light, the incident ray and the retroreflected ray are arranged to simulate the real conditions of illumination and nocturnal visibility of road signs marked on a road's surface from the driver of a motor vehicle; and that the measurement of the value or degree of retroreflectivity is executed directly on the sample in question, eliminating the need for a comparative sample and, in consequence, the need for zeroing the apparatus before each measurement, being also possible to vary the angle of inclination of the incident ray ($\alpha$) and the angle of inclination of the photo-electric cell in relation to the retroreflected ray which simulates the driver's angle of sight, and thus altering the value of the angle of divergence or phase displacement angle ($\beta$-$\alpha$) between the incident ray and the retroreflected ray, the angle ($\beta$) being the angle between the retroreflected ray and the horizontal.

3. A retroreflectometer in accordance with claims 1 or 2, wherein the optimum angles ($\alpha$), obtained experimentally, are 11°, 13.5° and 16°.

4. A retroreflectometer in accordance with claims 1 or 2, wherein the optimum time of the timer experimentally obtained in order to stabilize the reading of the retroreflectivity value is of 20 sec., and after this time the apparatus resets itself automatically.

5. A retroreflectometer in accordance with any one of claims 1 or 2, wherein the photosensitive measuring apparatus consists of a plurality of photo-electric cells (24) connected in series, each of which is provided to measure a portion of the intensity of the ray of retroreflected light, so as to ascertain a selective value for each single portion, such values being subsequently transduced into cumulative logical values, thus allowing a detailed survey to be made for the behavior of the sample.

6. A retroreflectometer in accordance with claim 1, characterized in that it is constructed in two separate sections or modules, one comprising the chamber with its photo-optical element and a battery of accumulators, and the other section, in the form of a portable control panel or console, comprising reading and control instruments.

7. An improved retroreflectometer in accordance with claim 1, which is fixed to a chassis that is open underneath and mounted telescopically on a trolley on roller or castors, so that it can be raised and lowered to enable the chamber to be in contact with the ground; the chassis being raised and lowered by means of a rack and sector gear, or hydraulic devices, that can be operated by means of a bar used to tow and steer the trolley.

* * * * *